(12) United States Patent
Vince

(10) Patent No.: US 9,994,970 B2
(45) Date of Patent: Jun. 12, 2018

(54) METHOD OF PRODUCING A SYNTHETIC DIAMOND

(71) Applicant: ECOTRICITY GROUP LIMITED, Gloucestershire (GB)

(72) Inventor: Dale Vince, Gloucestershire (GB)

(73) Assignee: ECOTRICITY GROUP LIMITED, Gloucestershire (GB)

( * ) Notice: Subject to any disclaimer, the term of this patent is extended or adjusted under 35 U.S.C. 154(b) by 0 days. days.

(21) Appl. No.: 15/015,992

(22) Filed: Feb. 4, 2016

(65) Prior Publication Data

US 2016/0230311 A1    Aug. 11, 2016

(30) Foreign Application Priority Data

Feb. 6, 2015    (GB) .................... 1501992.0

(51) Int. Cl.
*C30B 29/04*    (2006.01)
*C12P 5/02*    (2006.01)
(Continued)

(52) U.S. Cl.
CPC ............. *C30B 29/04* (2013.01); *B28D 5/00* (2013.01); *C01B 32/25* (2017.08); *C12P 5/023* (2013.01);
(Continued)

(58) Field of Classification Search
CPC .......... B28D 5/00; C01B 31/06; C01B 31/20; C07C 1/12; C12P 5/023; C25B 15/08; C25B 1/04; C25B 1/10; C25B 3/00; C25B 3/04; C30B 25/08; C30B 25/10; C30B 25/105; C30B 25/20; C30B 25/205; C30B 29/04
See application file for complete search history.

(56) References Cited

U.S. PATENT DOCUMENTS 3,852,180 A  *  12/1974  Gregory ................... C07C 1/12
                                                      204/246
4,490,232 A     12/1984  Lapeyre
(Continued)

FOREIGN PATENT DOCUMENTS

AU    2014200989 A1  *  10/2014
EP    0904825 A2     3/1999
(Continued)

OTHER PUBLICATIONS

Goeppert et al: "Air as the renewable carbon source of the future: an overview of C02 capture from the atmosphere", Energy & Environmental Science, vol. 5, No. 7, May 1, 2012 (May 1, 2012), p. 7833.
(Continued)

*Primary Examiner* — Hua Qi
(74) *Attorney, Agent, or Firm* — Lando & Anastasi, LLP

(57) ABSTRACT

A method of producing a synthetic diamond is disclosed, the method comprising: (a) capturing carbon dioxide from the atmosphere; (b) conducting electrolysis of water to provide hydrogen; (c) reacting the carbon dioxide obtained from step (a) with the hydrogen obtained from step (b) to produce methane; and (d) using the hydrogen obtained from step (b) and the methane obtained from step (c) to produce a synthetic diamond by chemical vapor deposition (CVD).

28 Claims, 2 Drawing Sheets

(51) Int. Cl.
| | |
|---|---|
| *C25B 1/04* | (2006.01) |
| *B28D 5/00* | (2006.01) |
| *C25B 1/10* | (2006.01) |
| *C30B 25/10* | (2006.01) |
| *C30B 25/20* | (2006.01) |
| *C30B 35/00* | (2006.01) |
| *C25B 15/08* | (2006.01) |
| *C25B 3/04* | (2006.01) |
| *C01B 32/25* | (2017.01) |
| *C01B 32/50* | (2017.01) |

(52) U.S. Cl.
CPC .............. *C25B 1/04* (2013.01); *C25B 1/10* (2013.01); *C25B 3/04* (2013.01); *C25B 15/08* (2013.01); *C30B 25/105* (2013.01); *C30B 25/205* (2013.01); *C30B 35/007* (2013.01); *C01B 32/50* (2017.08); *Y02E 50/343* (2013.01); *Y02E 60/366* (2013.01)

(56) References Cited

U.S. PATENT DOCUMENTS

| | | | |
|---|---|---|---|
| 4,958,590 | A | 9/1990 | Goforth |
| 2010/0242837 | A1 | 9/2010 | Goto et al. |
| 2010/0326135 | A1* | 12/2010 | Twitchen ............ C23C 16/27 63/26 |
| 2012/0302045 | A1* | 11/2012 | Yamada ............ C23C 14/0605 438/478 |
| 2013/0109074 | A1* | 5/2013 | Aines .................. B01D 53/14 435/188 |
| 2014/0322632 | A1* | 10/2014 | Sugimoto ............ C23C 18/08 429/532 |

FOREIGN PATENT DOCUMENTS

| | | |
|---|---|---|
| JP | 2005060137 A * | 3/2005 |
| WO | 2010010352 A1 | 1/2010 |
| WO | 2012110257 A1 | 8/2012 |
| WO | 2014154250 A1 | 10/2014 |
| WO | WO 2014154250 A1 * | 10/2014 ............ C07C 1/12 |

OTHER PUBLICATIONS

International Search Report and Written Opinion for corresponding International Application No. PCT/GB2016/050279 dated May 9, 2016.

Leung et al: "An overview of current status of carbon dioxide capture and storage technologies", Renewable and Sustainable Energy Reviews., vol. 39, Aug. 2, 2014 (Aug. 2, 2014), pp. 426-443.

Search Report for GB1501992.0 dated Aug. 24, 2015.

Yu, Cheng-Hsiu: "A Review of CO2 Capture by Absorption and Adsorption", Aerosol and Air Quality Research, Jan. 1, 2012 (Jan. 1, 2012).

* cited by examiner

US 9,994,970 B2

METHOD OF PRODUCING A SYNTHETIC DIAMOND

CROSS-REFERENCE TO RELATED APPLICATION

This application claims the benefit under 35 U.S.C. § 119 of United Kingdom Patent Application No. GB1501992.0, filed on Feb. 6, 2015 which is hereby incorporated by reference in its entirety for all purposes.

TECHNICAL FIELD

Aspects and embodiments relate to a method of producing a synthetic diamond. In particular, certain embodiments relate to a method of using carbon dioxide from direct air capture (DAC) and renewable energy to produce a synthetic diamond.

BACKGROUND

Carbon dioxide in the atmosphere accounts for a large proportion of the "enhanced greenhouse effect." Carbon dioxide concentrations in the atmosphere are increasing, due at least in part to the burning of fossil fuels. The increasing level of carbon dioxide in the atmosphere is a significant contributor to climate change.

The process of mining a diamond typically requires the burning of large quantities of fossil fuels and therefore the release of large volumes of carbon dioxide into the atmosphere. In particular, fossil-fuel-powered vehicles are used to transport the rock in which diamonds are found in a mine to the surface and then to a factory for processing. Very little diamond by weight or volume is found in the rock by comparison to the overall weight or volume of the rock, and the diamond that is yielded from the rock must be further cut and polished to produce a gem. Thus, the vehicles must carry a significant amount of weight and volume of rock to the factory in comparison to the finished gem which is yielded after processing at the factory. The processing of the rock at the factory is also typically energy-intensive, since the rock has to be crushed to release the diamonds. The burning of fossil fuels in mining, transporting and processing diamonds therefore releases an appreciable volume of carbon dioxide into the atmosphere. For example, the Ekati mine in Canada releases 65 kg (143 lb) of carbon dioxide per carat. (BHP Billiton 2008: Ekati mine emissions 195,179 metric tons of $CO_2$ equivalent, production 3,000,000 carats of rough diamonds.)

An object of one or more embodiments is to address one or more of these problems.

SUMMARY

According to a first aspect of the invention, there is provided a method of producing a synthetic diamond, the method comprising:
a) capturing carbon dioxide from the atmosphere;
b) conducting electrolysis of water to provide hydrogen;
c) reacting the carbon dioxide obtained from step (a) with the hydrogen obtained from step (b) to produce methane; and
d) using the hydrogen obtained from step (b) and the methane obtained from step c) to produce a synthetic diamond by chemical vapour deposition.

In some aspects, the method of producing a synthetic diamond comprises:

(a) capturing carbon dioxide from the atmosphere;
(b) performing electrolysis of water to provide hydrogen;
(c-1) electrochemically reacting the carbon dioxide obtained from step (a) with water to produce methane; and
(d) using the hydrogen obtained from step (b) and the methane obtained from step (c-1) to produce a synthetic diamond by chemical vapour deposition (CVD).

In accordance with certain aspects, step (a) may comprise capturing carbon dioxide using a nanotube gas separator.

According to some aspects, step (a) may comprise capturing carbon dioxide using a recyclable carbon dioxide sorbent or a polymer membrane gas separator.

According to another aspect, step (a) may comprise capturing carbon dioxide using an amine scrubber. Various amines are suitable for carbon dioxide capture. According to a further aspect, the amine scrubber may be monoethanolamine.

According to another aspect, step (a) may comprise capturing carbon dioxide using an amine-based sorbent material. Various amine-based sorbent materials are suitable for carbon dioxide capture. According to at least one aspect, capturing carbon dioxide using an amine-based sorbent material may be performed at a temperature of 25° C. or below. According to some aspects, capturing carbon dioxide using an amine-based sorbent material is performed at a temperature below 25° C.

According to some aspects, once carbon dioxide has been captured using a sorbent material, the captured carbon dioxide is desorbed from the sorbent material by applying heat to the sorbent. For example, the captured carbon dioxide may be subsequently released by heating the amine-containing sorbent material to a temperature above 25° C.

According to another aspect, step (a) may comprise capturing carbon dioxide using a mineral or a zeolite, which binds reversibly to carbon dioxide. According to a further aspect, the mineral or zeolite may comprise calcium oxide, serpentinite or molecular sieves.

According to certain aspects, step (a) may comprise capturing carbon dioxide using a caustic solution. According to a further aspect, the caustic solution may be calcium hydroxide solution, sodium hydroxide solution, potassium hydroxide solution, lithium hydroxide solution or soda lime.

In accordance with some aspects, step (a) may comprise capturing carbon dioxide using activated carbon or lithium peroxide.

In accordance with another aspect, step (a) may comprise capturing air. According to certain aspects, the air captured may be ambient air. In accordance with a further aspect, the carbon dioxide is not captured from flue gas.

According to various aspects, step (a) may comprise drying the air. In accordance with some aspects, a dessicant dryer may be used to dry the air. According to a further aspect, the air may be dried to a dew point of less than −70° C. According to another aspect, the air may be dried to a dew point of substantially −70° C. In accordance with some aspects, step (a) may comprise cooling the air to liquefy carbon dioxide in the air. According to a further aspect, cooling the air to liquefy carbon dioxide in the air may comprise compressing the air and then expanding the air. According to a further aspect, the steps of compression and then expansion of the air may be repeated. In accordance with a further aspect, the steps may be repeated three times. According to an even further aspect, the steps may be repeated four times.

According to various aspects, one or more features discussed above may be combined. For instance, in some aspects, carbon dioxide is captured using an amine-containing sorbent material at a temperature below 25° C., and the captured carbon dioxide is desorbed by applying heat to the sorbent material.

According to one or more aspects, step (b) may comprise conducting electrolysis of water using at least one solid oxide electrolysis cell (SOEC). According to a further aspect, the SOEC may be a solid oxide fuel cell that is arranged to use a solid oxide or ceramic electrolyte to produce oxygen and hydrogen gas. According to another aspect, when at least one SOEC is used for the electrolysis of water in step (b), the electrolysis may be conducted at a temperature of between 350 and 1000° C. According to a further aspect, the electrolysis may be conducted at a temperature of between 500 and 850° C.

In accordance with some aspects, step (b) may comprise conducting electrolysis of water using at least one polymer electrolyte membrane (PEM) cell. According to a further aspect, the PEM cell may be arranged to use a solid polymer electrolyte (SPE) to produce hydrogen. According to various aspects, when at least one PEM cell is used for the electrolysis of water in step (b), the electrolysis may be conducted at a temperature below 150° C. According to a further aspect, the electrolysis may be conducted at a temperature of 100° C. or below. According to an even further aspect, the electrolysis may be conducted at a temperature between 50 and 100° C.

According to certain aspects, step (b) may comprise conducting electrolysis of water using at least one alkaline electrolysis cell (AEC). According to a further aspect, the alkaline electrolysis cell (AEC) may comprise two electrodes arranged to operate in a liquid alkaline electrolyte solution. According to a further aspect, the liquid alkaline electrolyte solution may comprise potassium hydroxide, sodium hydroxide or potassium carbonate. In accordance with one or more aspects, when at least one AEC is used for the electrolysis of water in step (b), the electrolysis may be conducted at a temperature of between 50° C. and 300° C. According to a further aspect, the electrolysis may be conducted at a temperature between 150° C. and 250° C.

According to at least one aspect, the water may comprise rainwater, potable water, water recycled from elsewhere in the diamond-production process, and any combination of these. According to another aspect, step (b) may comprise filtering the water. According to another aspect, step (b) may comprise conducting reverse osmosis on the water. According to a further aspect, the reverse osmosis may be conducted so as to substantially purify the water. According to various aspects, step (b) may comprise distilling the water. According to other aspects, step (b) may comprise de-ionising the water.

The majority of hydrogen produced globally is from the cracking of methane. This is not an environmentally friendly way to generate hydrogen as the methane comes from natural gas sources. Electrolysis of water is the most environmentally-friendly method of producing hydrogen, particularly when the energy used for this process is renewable energy (as discussed further below).

At least one benefit of the processes disclosed herein is that a number of methane-production (methanation) methods may be used in step (c). These methane-production methods may, for instance, include thermochemical processes and biological processes and combinations of these processes. According to certain aspects, step (c) can be employed in conjunction with electrochemical processes for producing methane from water and carbon dioxide, which is discussed in relation to step (c-1) below.

In accordance with one or more aspects, step (c) may comprise reacting the carbon dioxide with the hydrogen according to the Sabatier reaction; in other words, according to the Sabatier process. The Sabatier process is one example of a thermochemical process and involves the reaction of hydrogen with carbon dioxide to produce methane and water, which is described by the following exothermic reaction:

$$CO_2+4H_2 \rightarrow CH_4+2H_2O+\text{energy}$$

According to at least one aspect, the reaction of step (c) may be carried out at a temperature between 100° C. and 800° C. According to a further aspect, the reaction may be carried out at a temperature between 150° C. and 600° C. According to a further aspect, the reaction may be carried out at a temperature between 250° C. and 450° C. According to another aspect, the reaction may be carried out at a temperature of substantially 250° C.

According to some aspects, the reaction of step (c) may be carried out at atmospheric pressure. According to other aspects, the reaction of step (c) may be carried out at a pressure above atmospheric pressure. According to a further aspect, the reaction of step (c) may be carried out at a pressure of 0.7 barg.

According to at least one aspect, at least a portion of the water produced from the Sabatier process may be recycled or otherwise used in the electrolysis process of step (b). In certain instances at least a portion of the water produced from the Sabatier process may be used alone or in combination with rainwater or any other source of water in the electrolysis process. This allows for an additional savings of resources.

According to certain aspects, the reaction of step (c) may be carried out in the presence of a catalyst. According to a further aspect, the catalyst may be a nickel-based catalyst, a ruthenium-based catalyst, a rhenium-based catalyst, a rhodium-based catalyst, or a cobalt-based catalyst. According to another aspect, the catalyst may comprise a mixture of a nickel-based catalyst and a ruthenium-based catalyst. In accordance with various aspects, the catalyst may be supported or unsupported. According to a further aspect, the catalyst may be supported on a support comprising an oxide. According to another aspect, the catalyst may be supported on a support comprising $TiO_2$, $SiO_2$, $MgO$ or $Al_2O_3$.

According to various aspects, the reaction of step (c) may be a biological process. For example, step (c) can be performed using methanogens. Methanogens are microorganisms that produce methane as a metabolic by-product in anoxic conditions. In some aspects, the methanogens are archaea, which are less sensitive to the environment they operate in. In accordance with some aspects, when the reaction of step (c) is performed using methanogens, the reaction may comprise reacting the carbon dioxide with the hydrogen according to the following reaction:

$$CO_2+4H_2 \rightarrow CH_4+2H_2O+\text{energy}$$

In other words, the reaction may be substantially the same as the Sabatier process, but may be a natural reaction. In accordance with a further aspect, the methanogens may be archaea or other prokaryotes. Step (c) may be carried out using conceivably any species of methanogen. In accordance with various aspects, the methanogens create methane as part of their respiration process, where carbon dioxide is converted into methane under conditions that are generally low temperature (~50° C.) and low pressure (atmospheric pressure or slightly above). According to various aspects, step (c) may comprise purifying the methane produced.

According to one or more aspects, step (c) can be conducted as step (c-1), which comprises the electrochemical formation of methane from carbon dioxide, captured in step (a), and water. Step (c-1) has the advantage that both input materials, carbon dioxide and water, are abundant natural resources. The electrochemical reaction below shows the reactants and a range of possible products that may be obtained when an electric current is applied to conduct such a reaction:

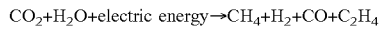

$$CO_2 + H_2O + \text{electric energy} \rightarrow CH_4 + H_2 + CO + C_2H_4$$

According to at least one aspect, the reaction of step (c-1) may be carried out at a temperature between 0° C. and 100° C. According to a further aspect, the reaction may be carried out at a temperature between 10° C. and 70° C. According to a further aspect, the reaction may be carried out at a temperature between 15° C. and 40° C. According to another aspect, the reaction may be carried out at a temperature of about 25° C.

According to at least one aspect, the reaction of step (c-1) may be carried out at a pressure that is above atmospheric pressure. According to a further aspect, the reaction may be carried out at a pressure of from 1 to 10 atm. According to an alternative aspect, the reaction may be carried out at a pressure below atmospheric pressure. According to another aspect, the reaction may be carried out at atmospheric pressure.

According to at least one aspect, the reaction of step (c-1) is carried out by providing electric energy in the form of direct current. According to a further aspect, the voltage of the direct current may be 1.0-5.0 V. According to another aspect, the voltage of the direct current may be 1.5-2.5 V. According to another aspect, the voltage of the direct current may be 1.8-2.2 V.

According to at least one aspect, the reaction of step (c-1) is carried out in the gaseous phase. According to a further aspect, the gas flow rate through the reactor is from 20 to 50 sccm.

According to at least one aspect, the reaction of step (c-1) is carried out in the presence of a catalyst. According to certain aspects, the catalyst is a metal catalyst. According to a further aspect, the catalyst is a nickel-based catalyst. According to a further aspect, the metal catalyst is supported on a support material.

According to at least one aspect, the water may comprise rainwater, potable water, water recycled from elsewhere in the diamond-production process, and combinations of these.

As mentioned above, step (c) can also be conducted using a combination of one or more thermochemical processes and biological processes. According to another aspect, one or more thermochemical processes and biological processes of step (c) can be carried out in combination with the electrochemical process of step (c-1) in order to produce methane by different reactions. In instances where one or more processes are used in combination, the processes can, for instance, be used in series, in parallel, or a mixture of series and parallel.

According to various aspects, the methane produced by step (c) or step (c-1) may be purified using a pressure swing adsorption technique. In accordance with some aspects, step (c) or step (c-1) may comprise using molecular sieves to remove oxygen. According to certain aspects, step (c) or step (c-1) may comprise using zeolites to remove at least one of carbon dioxide, nitrogen, and water. In a similar manner as discussed above with reference to the Sabatier process, according to at least one aspect at least a portion of the water produced as a result of the methanation process using the methanogens may be recycled or otherwise used in the electrolysis process of step (b).

In accordance with certain aspects, the methane may be purified using cryogenics. According to one aspect, step (c) or step (c-1) may comprise using membranes to remove nitrogen and $CO_2$. According to another aspect, step (c) or step (c-1) may comprise using desiccant drying to remove water.

According to some aspects, step (c) or step (c-1) may comprise using an amine gas treater to remove sulphide impurities.

Chemical vapour deposition (CVD) allows films of synthetic diamond to be grown over large areas of substrate with control over the properties of the diamond produced.

In accordance with one or more aspects, the CVD of step (d) may be carried out at a pressure of between 0.5 kPa and 100 kPa. According to a further aspect the CVD step may be carried out at a pressure of between 1 kPa and 50 kPa. According to an even further aspect, the CVD step may be carried out at a pressure of substantially 40 kPa.

According to various aspects, the CVD of step (d) may be carried out at a temperature between 600° C. and 1200° C. According to a further aspect, the CVD step may be carried out at a temperature between 700° C. and 1000° C. According to another aspect, the CVD step may be carried out at a temperature of substantially 950° C. According to certain aspects, the ratio of hydrogen to methane used in step (d) may be about 5:1. According to other aspects, the ratio of hydrogen to methane used in step (d) can be from 1:1 to 9:1, from 1:1 to 8:1, or from 5:1 to 8:1.

According to at least one aspect, the CVD of step (d) may be carried out on a substrate. In accordance with certain aspects, the substrate may comprise diamond, silicon, tungsten, molybdenum, silicon carbide, silicon nitride, quartz glass or cemented carbide.

In accordance with one or more aspects, the CVD of step (d) may be carried out using a microwave plasma CVD machine.

According to certain aspects, step (a) may be performed before step (b). According to other aspects, step (b) may be performed before step (a) or substantially simultaneously with step (a).

In accordance with some aspects, the method may comprise an additional step, after step (d), of annealing the synthetic diamond. According to a further aspect, the step of annealing the synthetic diamond may be carried out in a High Pressure High Temperature (HPHT) press.

In accordance with at least one aspect, the method may comprise a step, after step (d), and, in embodiments in which the synthetic diamond is annealed, after the step of annealing the synthetic diamond, of cutting and/or polishing the diamond produced in step (d) to produce a gem-quality diamond.

According to another aspect, the method may comprise the step of reacting oxygen produced from the electrolysis of the water in step (b) with carbon produced by the chemical vapour deposition in step (d) to produce carbon dioxide. According to a further aspect, the method may comprise reacting the carbon dioxide obtained from this step with the hydrogen obtained from step (b) to produce methane. According to another aspect, the method may comprise adding the carbon dioxide to the carbon dioxide captured from the atmosphere prior to step (c).

In accordance with certain aspects, the method may comprise separating water produced from the reaction of step (c) from the methane produced by that reaction. According to a further aspect, the separation of the water from the methane may be conducted by centrifugation, condensation or adsorption. According to another aspect, the method may comprise electrolysing the water to provide hydrogen.

According to at least one aspect, the method may comprise using energy from at least one renewable source to perform at least one of the steps. According to a further aspect, the method may comprise using energy from at least one renewable source to perform the electrolysis. According to another aspect, the method may comprise using energy from at least one renewable source to perform each of the steps. As used herein, the term "renewable source" when used in reference to energy sources generally refers to one or more technologies that utilize replenishable energy sources such as energy from water, wind, and the sun. For example, according to various aspects, the at least one renewable source may comprise wind power. According to another aspect, the at least one renewable source may comprise solar power. According to yet another aspect, the at least one renewable source may comprise wave power or tide power.

In accordance with embodiments in which the diamond produced in step (b) is cut and/or polished to produce a gem-quality diamond, in which energy from at least one renewable source is used to perform each of the steps, and in which the water in step (b) is rainwater, up to 230 times less carbon dioxide is released in the production of a gem-quality diamond than the production of such a diamond from mining. According to certain aspects, approximately 40 times less carbon dioxide is released than in the production of a gem-quality diamond using the process which releases the next-least quantity of carbon dioxide. It is estimated that if the global demand for diamonds (124 million carats in 2011) were switched to diamonds produced using this method, carbon dioxide emissions would be reduced by nearly 8 million tonnes per year.

BRIEF DESCRIPTION OF THE DRAWINGS

Specific embodiments will now be described by way of example only, and with reference to the accompanying drawings in which.

DETAILED DESCRIPTION

Overview

Figure 1:
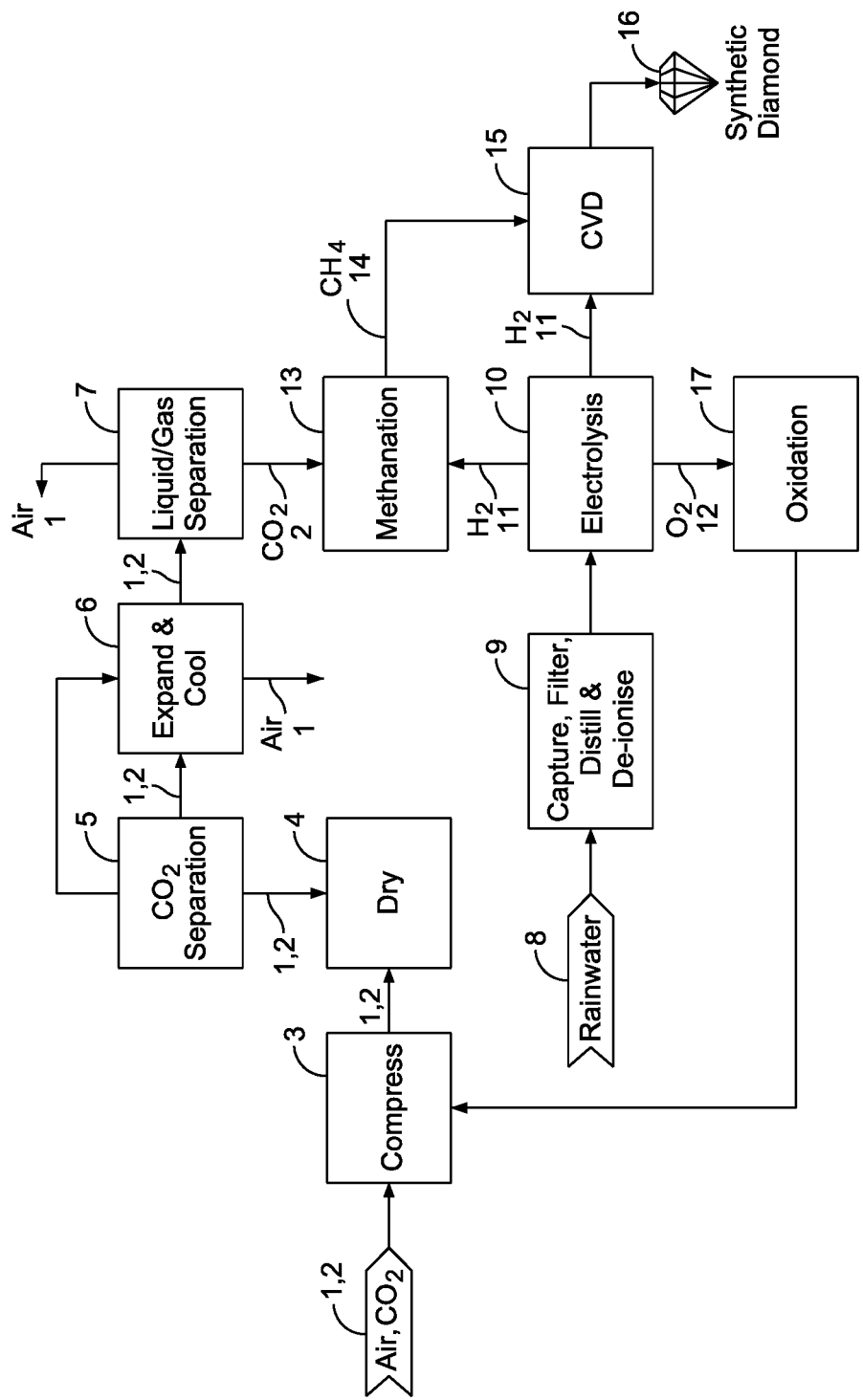
FIG. 1 is a flow diagram of an embodiment of the method of producing a synthetic diamond.

With reference to FIG. 1, an example of the method for manufacturing diamonds will now be described in overview.

First, carbon dioxide 2 is captured from the atmosphere; that is, carbon dioxide 2 is captured from air 1. To capture carbon dioxide 2, the following process can be used. Air 1, which has carbon dioxide 2 in it, is compressed 3 and then dried 4. Carbon dioxide 2 is then separated 5 from the air 1 (although some air 1 will remain) and the separated carbon dioxide 2 and remaining air 1 are compressed and expanded to cool 6 the carbon dioxide 2. The carbon dioxide 2 and remaining air 1 are compressed and expanded 7, such that the carbon dioxide 2 liquefies. The remaining air 1 is evacuated.

Second, water is electrolysed to provide hydrogen 11. In one embodiment, the water is rainwater 8. To produce hydrogen 11 from the rainwater 8, the following process is used. Rainwater 8 is captured, filtered, distilled and de-ionised 9. The resulting filtered and de-ionised rainwater 8 is then electrolysed 10 to produce hydrogen 11 and oxygen 12.

Third, carbon dioxide 2 obtained from the first step is reacted with the hydrogen 11 obtained from the second step to produce methane 14 (methanation 13). The methanation 13 process is as follows. The hydrogen 11 and carbon dioxide 2 are reacted according to the Sabatier reaction, described by the following equation:

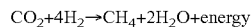

The products are methane 14 and water 8. As noted throughout this application, the reaction of carbon dioxide with hydrogen to form methane can also be conducted using a biological process, which can involve organisms known as methanogens. In further aspects, methanation can be conducted by carried out by reacting carbon dioxide with water to produce methane. In reference to FIG. 1, methanation 13 may be carried out by reacting carbon dioxide 2 with water 8 rather than processing water 8 through an electrolysis process 10 to produce hydrogen 11.

Fourth, the hydrogen 11 obtained from the second step and the methane 14 obtained from the third step are used to produce a synthetic diamond 16 using CVD 15.

Direct Air Capture of Carbon Dioxide

Figure 2:
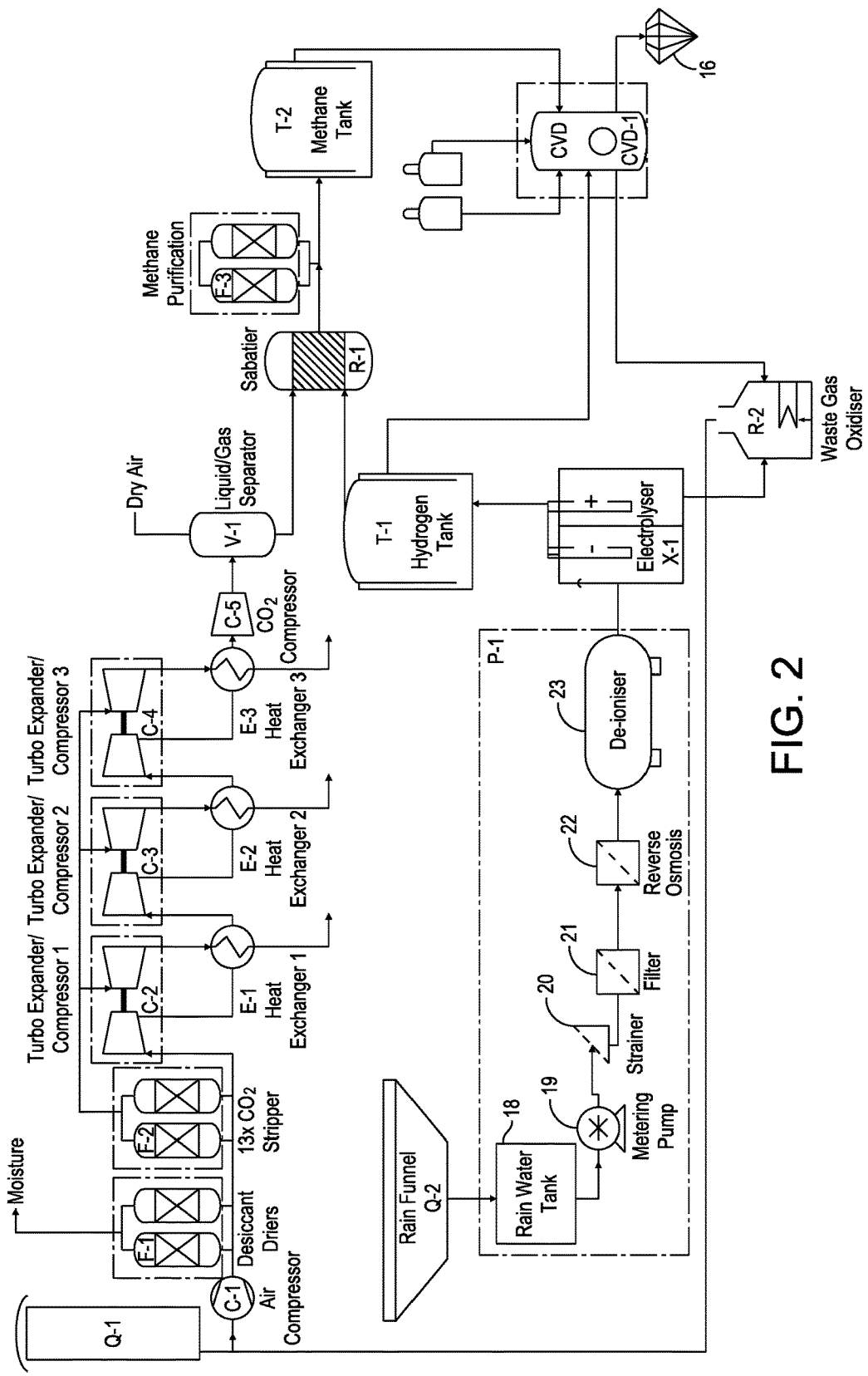
FIG. 2 shows, schematically, an apparatus for use with the method.

Referring to FIGS. 1 and 2, the process of capturing carbon dioxide 2 as described above in overview above will now be described in more detail. An example of an apparatus used for this process will also be described.

The step of producing a synthetic diamond 16 using CVD requires high-purity carbon dioxide 2. In one embodiment, the purity required is 99.9999%. The concentration of carbon dioxide in the atmosphere is around 400 ppm. The process of capturing carbon dioxide 2 from the air 1 therefore requires the concentration of carbon dioxide 2 to be increased. Air 1, with carbon dioxide 2 in it, is drawn from a column Q-1 into a compressor C-1. The air 1 and carbon dioxide 2 are compressed 3 in the compressor C-1 (shown in FIG. 2). In one example, the compressor C-1 is a high purity oil-free air compressor. The compressor C-1 increases the pressure of the air 1 and carbon dioxide 2 to a gauge pressure of around 12 barg.

Next, the air 1 and carbon dioxide 2 are dried 3. A desiccant dryer F-1 can be used. In this embodiment, the air 1 and carbon dioxide 2 are dried 3 to a dew point of −70° C.

Carbon dioxide 2 is then separated 5 from the air 1 (although some air 1 will remain), for example, using a nanotube gas separator. In this embodiment, the nanotube gas separator is a nanotube 13X zeolite adsorption stripper F-2. In this embodiment, the nanotube 13X zeolite adsorption stripper F-2 strips out the carbon dioxide 2 from at least 80% of the other air 1 components. The resulting gas stream is at ambient pressure and rich in carbon dioxide 2.

The gas stream of air 1 and carbon dioxide 2 is then passed through a series of turbo compressor-expanders C-2, C-3, C-4. Each turbo compressor-expander C-2, C-3, C-4 compresses the air 1 and carbon dioxide 2 to condense the carbon dioxide 2 and then expands the air 1 and carbon dioxide 2 to chill 6 them in a respective heat exchanger E-1, E-2, E-3. In this embodiment, there are three turbo compressor/expanders C-2, C-3, C-4, each with a heat exchanger E-1, E-2, E-3 through which the stream of air 1 and carbon dioxide 2 flows before it is again compressed and expanded. However, it is to be appreciated that more or fewer turbo compressor-expanders can be used. The turbo compressor-expanders C-2, C-3, C-4 are such as those used in automotive technology. According to various aspects, step (a) may comprise drying the air.

In reference to the turbo compressor-expander device discussed above, in accordance with some aspects, capturing carbon dioxide from the atmosphere may comprise cooling the air to liquefy carbon dioxide in the air. For example, cooling the air to liquefy carbon dioxide in the air may comprise compressing the air and then expanding the air, such as by using one or more of the turbo compressor-expander devices described above. According to a further aspect, the steps of compression and then expansion of the air may be repeated. In accordance with a further aspect, the steps may be repeated three times. According to an even further aspect, the steps may be repeated four times.

Next, liquid/gas separation 7 is used to separate carbon dioxide 2 from the stream of air 1 and carbon dioxide 2. The carbon dioxide 2 and remaining air 1 are compressed in a compressor C-5. Then, they are expanded in a tank V-1, such that the carbon dioxide 2 liquefies. In this embodiment, the carbon dioxide 2 is at a temperature of around −40° C. and a pressure of over 10 bar. The remaining air 1 is evacuated.

The liquid carbon dioxide 2 is warmed and returned into its gaseous form prior to being fed into a Sabatier reactor R-1 for methanation, as described further below.

Carbon dioxide 2 can also be captured and prepared for methanation 13 by other means. For instance, carbon dioxide 2 can be captured on an amine-containing sorbent material at a temperature below 25° C. For instance, the sorbent material may be heated (to a temperature above 25° C.) to release the captured carbon dioxide gas. In the context of FIG. 1, this would process carbon dioxide 2 to methanation 13. In the context of FIG. 2, this would process from column Q-1 to tank V-1 following different processing steps than those outlined in FIG. 2 between column Q-1 and tank V-1.

Hydrogen Generation

With continued reference to FIGS. 1 and 2, the second step of electrolysing water 8 to provide hydrogen 11, will now be described in more detail. An example of the apparatus used in this step will also be described.

Rainwater 8 is collected via a rainwater 8 funnel Q-2 and stored in a tank 18. In a variation of this process, water may be collected in tank 18 from a source other than rainwater, such as potable water, and/or water recycled from elsewhere in the overall diamond-production process. The water 8 is transferred via a metering pump 19 connected to the tank 18 into a strainer 20. The metering pump 19 operates at low pressure. In this embodiment, the pressure at which the metering pump 19 operates is about 0.5 barg. The water 8 passes through the strainer 20 and is strained by the strainer 20. Next, the water 8 passes through a filter 21 which filters the water 8 relatively coarsely. From the filter 21, the water 8 enters a reverse osmosis purification unit 22, which further purifies the water 8 using reverse osmosis. Next, the water 8 is distilled in a still (not shown) and de-ionised in a de-ioniser 23. In an alternative process, water 8 can be purified by reverse osmosis.

From the de-ioniser 23, the water passes to an electrolyser X-1. The electrolyser X-1 is powered by renewable energy. For example, the electrolyser X-1 can be powered by wind, solar, wave, tide, or geothermal energy. The electrolyser X-1 splits the water 8 into hydrogen 11 and oxygen 12 via an electrolysis 10 process. In this embodiment, the resulting hydrogen 11 is at about 99.999% purity. The oxygen 12 is taken off into a waste gas oxidiser R-2, to be used in a waste gas recovery process, as will be described further below. The hydrogen 11 is taken into a hydrogen storage tank T-1.

The hydrogen storage tank T-1 is a specialist lab equipment tank that stores the hydrogen 11 input at 99.999% purity and returns the hydrogen 11 at 99.9999% purity. The tank T-1 is a container containing solid metal hydride. In this embodiment, the solid metal hydride is an AB5-type alloy. Pressure is regulated using let-down valves from the stored pressure, which in one example can be as high as 10 barg.

In accordance with some aspects, electrolysis of water may be performed using at least one polymer electrolyte membrane (PEM) cell. According to a further aspect, the PEM cell may be arranged to use a solid polymer electrolyte (SPE) to produce hydrogen. According to various aspects, when at least one PEM cell is used for the electrolysis of water, the electrolysis may be conducted at a temperature below 150° C. According to a further aspect, the electrolysis may be conducted at a temperature of 100° C. or below. According to an even further aspect, the electrolysis may be conducted at a temperature between 50 and 100° C.

Methanation

As discussed above, the third step of the present method for the manufacture of a synthetic diamond involves the reaction of the carbon dioxide obtained from the first step with the hydrogen obtained from the second step to produce methane. This process, and the apparatus used for it, will now be described in more detail, with continued reference to FIGS. 1 and 2.

Carbon dioxide 2 obtained from the first step is stored, as described above, in a tank V-1. Hydrogen 11 from the second step is stored, as described above, in a hydrogen storage tank T-1. The carbon dioxide 2 and hydrogen 11 are drawn from these tanks V-1, T-1 into a Sabatier reactor R-1. In the Sabatier reactor R-1, the carbon dioxide 2 is reacted with the hydrogen 11 to produce methane 14 (methanation 13). The hydrogen 11 and carbon dioxide 2 are reacted according to the Sabatier reaction, described by the following equation:

$$CO_2 + 4H_2 \rightarrow CH_4 + 2H_2O + \text{energy}$$

According to certain aspects, the reaction may be carried out in the presence of a catalyst. In one embodiment, a Ruthenium catalyst is used. The reaction takes place at 250° C. and around 0.7 barg. Under these conditions, over 95% of the carbon dioxide 2 is converted, with substantially 100% selectivity of methane 14. That is, over 95% of the carbon dioxide 2 is converted exclusively to methane, without appreciable conversion of carbon dioxide 2 to any other product. According to at least one aspect, the reaction of may be carried out at a temperature between 100° C. and 800° C. According to a further aspect, the reaction may be carried out at a temperature between 150° C. and 600° C. According to a further aspect, the reaction may be carried out at a temperature between 250° C. and 450° C. According to another aspect, the reaction may be carried out at a temperature of substantially 250° C.

According to other aspects, the catalyst may be a nickel-based catalyst, a rhenium-based catalyst, a rhodium-based catalyst, or a cobalt-based catalyst, or any combination thereof. According to another aspect, the catalyst may comprise a mixture of a nickel-based catalyst and a ruthenium-based catalyst. In accordance with various aspects, the catalyst may be supported or unsupported. According to a further aspect, the catalyst may be supported on a support comprising an oxide. According to another aspect, the catalyst may be supported on a support comprising $TiO_2$, $SiO_2$, $MgO$ or $Al_2O_3$.

According to various aspects, the methanation reaction may be performed using methanogens. As discussed above, methanogens are microorganisms that produce methane as a metabolic by-product in anoxic or anaerobic conditions. In accordance with some aspects, when methanation is performed using methanogens, the reaction may comprise reacting the carbon dioxide with the hydrogen according to the following reaction:

$$CO_2 + 4H_2 \rightarrow CH_4 + 2H_2O + \text{energy}$$

In other words, the reaction may be substantially the same as the Sabatier process, but may be a natural reaction. In accordance with a further aspect, the methanogens may be archaea or other prokaryotes. Methanation may be carried out using conceivably any species of methanogen. In accordance with various aspects, the methanogens create methane as part of their respiration process, where carbon dioxide is converted into methane under conditions that are generally low temperature (−50° C.) and low pressure (atmospheric pressure or slightly above).

As explained above, according to various aspects, step (c-1) may include producing methane by the electrochemical reaction of water with carbon dioxide, instead of, or in addition to, the reaction of carbon dioxide with hydrogen obtained by the electrolysis of water. For example, in reference to FIGS. 1 and 2, electrochemical methanation is conducted using carbon dioxide 2 that has been stored in tank V-1, and purified water. The water can, for example, be purified in accordance with the processes described above (e.g., the subsection titled "Hydrogen Generation") or by reverse osmosis.

According to various aspects, the purified water and carbon dioxide may be fed to one or more electrochemical cells in the gaseous phase at a flow rate of 20-50 sccm. According to another aspect, the electrochemical cell may be powered by direct current at 1.8-2.2 V and may contain a catalyst comprising nickel.

Referring back to FIGS. 1 and 2, the methane 14 produced is then purified in a methane purification apparatus F-3. This apparatus F-3 purifies the methane 14 by removing any impurities, including the water 8 that is also a product of the Sabatier process or that is present as an unreacted input material for the electrochemical process. In this embodiment, the water 8 is collected via centrifugation, although condensation or an adsorption method can be used as alternatives. In this embodiment, the water 8 is added to (this is not shown) the water 8 that is electrolysed 10 in the electrolyser X-1 to be used for the creation of more hydrogen 11. The methane 14 is stored in a methane tank T-2, ready for use.

According to certain aspects, and within the context of the electrochemical methanation process, hydrogen gas produced as a by-product may be fed to the CVD diamond manufacture step as a co-reagent. Hydrogen gas produced as a by-product of the electrochemical methanation process may also be fed to the thermochemical and/or biological methanation steps, if present, in order to react with carbon dioxide to produce methane.

According to various aspects, the methane may be purified using a pressure swing adsorption technique. In accordance with some aspects, methanation may comprise using molecular sieves to remove oxygen. According to certain aspects, methanation may comprise using zeolites to remove at least one of carbon dioxide, nitrogen, and water. In a similar manner as discussed above with reference to the Sabatier process, according to at least one aspect at least a portion of the water produced as a result of the methanation process using the methanogens may be recycled or otherwise used in the electrolysis process.

In accordance with certain aspects, the methane may be purified using cryogenics. According to one aspect, methanation may comprise using membranes to remove nitrogen and $CO_2$. According to another aspect, methanation may comprise using desiccant drying to remove water. According to some aspects, methanation may comprise using an amine gas treater to remove sulphide impurities.

CVD Diamond Manufacture

The fourth step of the present method for the manufacture of a synthetic diamond 16 comprises utilising the hydrogen 11 obtained from the second step and the methane 14 obtained from the third step, to produce a synthetic diamond 16 using a CVD process 15. This CVD process 15 in the context of the present embodiment, and the apparatus that is used to conduct the CVD process 15 will now be described, with continued reference to FIGS. 1 and 2.

In one embodiment, the aim is to produce gem quality diamonds suitable for the jewellery market. The hydrogen 11 and the methane 14 are drawn into a CVD diamond machine CVD-1 from their respective tanks T-1, T-2. In one embodiment, the CVD diamond machine is a microwave plasma CVD machine. The gas mixture fed into the CVD diamond machine CVD-1 is at a ratio of about 5:1 hydrogen:methane. A microwave CVD process 15 is used to make a gem-quality single crystal diamond 16. In this embodiment, the CVD takes place at a pressure of 40 kPa (300 Torr) and a temperature of around 950° C. A power source of less than 50 kW produces a plasma zone on a diamond substrate. For example, the diamond substrate may comprise a diamond seed crystal that may then be used as the initial base for diamond crystal growth. Carbon drops out onto the lattice of the substrate to grow a diamond 16 that is ready for finishing.

In one embodiment, negatively-charged nitrogen inclusions are used to create green-coloured diamonds. In other embodiments, other dopants may be used to create other colours of diamonds.

In this embodiment, oxygen 12 is also purged from the CVD diamond machine CVD-1 to stop the formation of soot. This oxygen 12, along with carbon emissions from the machine, is sent to the waste gas oxidiser R-2. As discussed above, oxygen 12 from the electrolysis 10 process is also sent to the waste gas oxidiser R-2. In the waste gas oxidiser R-2, oxidation 17 of the carbon occurs, producing further carbon dioxide 2. According to one example, this carbon dioxide is added to the column Q-1 to increase the concentration of carbon dioxide 2 in the carbon dioxide 2 capture process. Remaining gases are made safe before emission to the atmosphere. According to another example, the carbon dioxide is reacted with the hydrogen obtained from the electrolysis process to produce methane.

In accordance with one or more aspects, the CVD process may be carried out at a pressure of between 0.5 kPa and 100 kPa. According to a further aspect the CVD step may be carried out at a pressure of between 1 kPa and 50 kPa. According to an even further aspect, the CVD step may be carried out at a pressure of substantially 40 kPa.

According to various aspects, the CVD process may be carried out at a temperature between 600° C. and 1200° C. According to a further aspect, the CVD step may be carried out at a temperature between 700° C. and 1000° C. According to another aspect, the CVD step may be carried out at a temperature of substantially 950° C. According to certain aspects, the ratio of hydrogen to methane used in the CVD process may be substantially 5:1.

According to at least one aspect, the CVD process may be carried out on a substrate. In accordance with certain aspects, the substrate may comprise diamond, silicon, tungsten, molybdenum, silicon carbide, silicon nitride, quartz glass or cemented carbide.

In accordance with one or more aspects, the CVD process may be carried out using a microwave plasma CVD machine.

Diamond Processing

In a final step (not shown) the diamond 16 is processed to gem quality by cutting and polishing.

In accordance with some aspects, after CVD processing, the synthetic diamond may be annealed. According to one example, the step of annealing the synthetic diamond may be carried out in a High Pressure High Temperature (HPHT) press.

In accordance with at least one aspect, the synthetic diamond may be cut and polished after the annealing step is performed to produce a gem-quality diamond.

According to at least one aspect, one or more of the processes discussed herein may include using energy from at least one renewable source. For example, electrolysis may comprise using energy from at least one renewable source. Thus, one or more technologies that utilize replenishable energy sources such as energy from water, wind, and the sun may be used to perform at least one of the processes discussed herein (i.e., carbon dioxide capture, electrolysis, methanation, CVD diamond formation). For example, according to various aspects, the at least one renewable source may comprise wind power, solar power, wave power, tide power, and/or geothermal power. According to a further aspect, renewable energy may be used to perform each of the processes discussed herein.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A method of producing a synthetic diamond, the method comprising:
   (a) capturing carbon dioxide from an atmosphere;
   (b) performing electrolysis of water to provide hydrogen;
   (c-1) electrochemically reacting the carbon dioxide obtained from step (a) with water to produce methane; and
   (d) using the hydrogen obtained from step (b) and the methane obtained from step (c-1) to produce the synthetic diamond by chemical vapour deposition (CVD); and
   (e) reacting oxygen produced from the electrolysis of the water in step (b) with carbon emissions produced by the chemical vapour deposition in step (d) to produce carbon dioxide.

2. The method of claim 1, wherein step (a) comprises capturing carbon dioxide using a nanotube gas separator.

3. The method of claim 1, wherein step (a) comprises cooling air to liquefy carbon dioxide in the air.

4. The method of claim 3, wherein cooling the air to liquefy carbon dioxide in the air comprises compressing the air and then expanding the air.

5. The method of claim 4, wherein the steps of compressing the air and then expanding the air are repeated.

6. The method of claim 5, wherein the steps are repeated three times.

7. The method of claim 1, wherein step (a) comprises capturing carbon dioxide using an amine-containing sorbent-material.

8. The method of claim 7, wherein capturing carbon dioxide using the amine-coated sorbent-material is conducted at a temperature below 25° C.

9. The method of claim 8, wherein the captured carbon dioxide is subsequently released by heating the amine-containing sorbent material to a temperature above 25° C.

10. The method of claim 1, wherein step (b) comprises performing the electrolysis of water using at least one polymer electrolyte membrane (PEM) cell.

11. The method of claim 10, wherein the electrolysis is performed at a temperature below 150° C.

12. The method of claim 1, wherein step (c-1) is conducted in the presence of a metal catalyst.

13. The method of claim 12, wherein the metal catalyst is a nickel-based catalyst.

14. The method of claim 1, wherein step (c-1) is conducted with a direct current.

15. The method of claim 1, wherein the CVD is carried out at a pressure of between 0.5 kPa and 100 kPa.

16. The method of claim 15, wherein the CVD is carried out at a pressure of substantially 40 kPa.

17. The method of claim 1, wherein the CVD is carried out at a temperature between 700° C. and 1000° C.

18. The method of claim 17, wherein the CVD is carried out at a temperature of substantially 950° C.

19. The method of claim 1, wherein a ratio of hydrogen to methane used in step (d) is in a range of from 1:1 to 9:1.

20. The method of claim 19, wherein the ratio of hydrogen to methane used in step (d) is about 5:1.

21. The method of claim 1, wherein the CVD is carried out on a substrate comprising diamond.

22. The method of claim 1, further comprising reacting the carbon dioxide obtained from step (e) with the hydrogen obtained from step (b) to produce methane.

23. The method of claim 1, wherein the method further comprises using energy from at least one renewable source to perform at least one of the steps (a)-(d).

24. The method of claim 23, wherein the method further comprises using energy from at least one renewable source to perform the electrolysis.

25. The method of claim 1, wherein the water used in step (b) comprises rainwater.

26. The method of claim 1, wherein the water used in step (c-1) comprises rainwater.

27. The method of claim 1, wherein the method further comprises an additional step, after step (d), of annealing the synthetic diamond.

28. The method of claim 1, wherein the method further comprises an additional step of at least one of cutting and polishing the diamond produced in step (d).

* * * * *